United States Patent
Scopton et al.

(10) Patent No.: US 11,484,594 B2
(45) Date of Patent: *Nov. 1, 2022

(54) DEVICES AND METHODS AND AGENT-ASSISTED MEDICAL PROCEDURES

(71) Applicant: Boston Scientific Scimed, Inc., Maple Grove, MN (US)

(72) Inventors: Paul Scopton, Winchester, MA (US); Samuel Zhong, Shrewsbury, MA (US); Yem Chin, Burlington, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,418

(22) Filed: Dec. 22, 2021

(65) Prior Publication Data

US 2022/0111051 A1  Apr. 14, 2022

Related U.S. Application Data

(63) Continuation of application No. 17/177,779, filed on Feb. 17, 2021, which is a continuation of application
(Continued)

(51) Int. Cl.
*A61K 47/10* (2017.01)
*A61L 26/00* (2006.01)
(Continued)

(52) U.S. Cl.
CPC .......... *A61K 47/10* (2013.01); *A61B 17/3478* (2013.01); *A61L 26/008* (2013.01); *A61L 27/52* (2013.01); *A61B 17/22012* (2013.01); *A61B 2017/00269* (2013.01)

(58) Field of Classification Search
CPC ............... A61K 47/10; A61B 17/3478; A61B 17/22012; A61B 2017/00269; A61L 26/008; A61L 27/52
See application file for complete search history.

(56) References Cited

U.S. PATENT DOCUMENTS

| 5,843,156 A | 12/1998 | Slepian et al. |
| 6,165,201 A | 12/2000 | Sawhney et al. |
(Continued)

FOREIGN PATENT DOCUMENTS

EP  1407791 A1  4/2004

*Primary Examiner* — Theodore J Stigell
(74) *Attorney, Agent, or Firm* — Seager, Tufte & Wickhem, LLP

(57) ABSTRACT

Various embodiments of bulking or cushioning agents or material and related medical devices and methods are disclosed. For example, a method of performing a medical procedure in a tract of a body may include injecting a material in a liquid phase proximate a target site between a first tissue layer and a second tissue layer, allowing the material to transition from the liquid phase to the gel phase in response to a raise in temperature of the material to approximately at or above the predetermined temperature, and performing a surgical procedure on the target site. The material may have the liquid phase at temperatures below a predetermined temperature and a gel phase at temperature approximately at or above the predetermined temperature.

20 Claims, 2 Drawing Sheets

Related U.S. Application Data

No. 16/823,979, filed on Mar. 19, 2020, now Pat. No. 10,933,138, which is a continuation of application No. 15/938,991, filed on Mar. 28, 2018, now Pat. No. 10,617,762, which is a continuation of application No. 14/486,783, filed on Sep. 15, 2014, now Pat. No. 9,956,286, which is a continuation of application No. 13/609,822, filed on Sep. 11, 2012, now Pat. No. 8,864,738, which is a continuation of application No. 13/024,642, filed on Feb. 10, 2011, now Pat. No. 8,282,621, which is a continuation of application No. 11/231,293, filed on Sep. 21, 2005, now Pat. No. 7,909,809.

(60) Provisional application No. 60/612,797, filed on Sep. 27, 2004.

(51) Int. Cl.
*A61L 27/52* (2006.01)
*A61B 17/34* (2006.01)
*A61B 17/00* (2006.01)
*A61B 17/22* (2006.01)

(56) References Cited

U.S. PATENT DOCUMENTS

| | | |
|---|---|---|
| 6,251,064 B1 | 6/2001 | Silverman et al. |
| 6,282,621 B1 | 8/2001 | Parsons et al. |
| 6,319,260 B1 | 11/2001 | Yamamoto |
| 6,478,775 B1 | 11/2002 | Galt et al. |
| 6,488,659 B1 | 12/2002 | Rosenman |
| 6,514,534 B1 | 2/2003 | Sawhney |
| 6,547,776 B1 | 4/2003 | Gaiser et al. |
| 6,613,037 B2 | 9/2003 | Khosravi et al. |
| 6,632,457 B1 | 10/2003 | Sawhney |
| 6,777,000 B2 | 8/2004 | Ni et al. |
| 6,818,018 B1 | 11/2004 | Sawhney |
| 7,449,020 B2 | 11/2008 | Edwards et al. |
| 7,909,809 B2 * | 3/2011 | Scopton ............ A61L 26/008 604/506 |
| 7,963,287 B2 | 6/2011 | Lanphere et al. |
| 8,282,621 B2 * | 10/2012 | Scopton ............ A61K 47/10 606/45 |
| 8,864,738 B2 * | 10/2014 | Scopton ............ A61B 17/3478 604/506 |
| 9,956,286 B2 * | 5/2018 | Scopton ............ A61L 26/008 |
| 10,933,138 B2 * | 3/2021 | Scopton ............ A61K 47/10 |
| 2001/0046518 A1 | 11/2001 | Sawhney |
| 2002/0082636 A1 | 6/2002 | Sawhney et al. |
| 2002/0106409 A1 | 8/2002 | Sawhney et al. |
| 2002/0119116 A1 * | 8/2002 | Sahatjian ............ A61M 5/178 604/113 |
| 2003/0012734 A1 | 1/2003 | Pathak et al. |
| 2003/0195464 A1 | 10/2003 | Sahatjian et al. |
| 2003/0211073 A1 | 11/2003 | Goupil et al. |
| 2004/0029994 A1 | 2/2004 | Cheng et al. |
| 2004/0094162 A1 | 5/2004 | Noyes |

* cited by examiner

DEVICES AND METHODS AND AGENT-ASSISTED MEDICAL PROCEDURES

CROSS REFERENCE TO RELATED APPLICATIONS

This application is a continuation of Ser. No. 17/177,779, filed Feb. 17, 2021, which is a continuation of U.S. patent application Ser. No. 16/823,979, filed Mar. 19, 2020, now granted as U.S. Pat. No. 10,933,138, which is a continuation of U.S. patent application Ser. No. 15/938,991, filed Mar. 28, 2018, now granted as U.S. Pat. No. 10,617,762, which is a continuation of U.S. patent application Ser. No. 14/486,783, filed Sep. 15, 2014, now granted as U.S. Pat. No. 9,956,286, which is a continuation of U.S. patent application Ser. No. 13/609,822, filed Sep. 11, 2012, now granted as U.S. Pat. No. 8,864,738, which is a continuation of U.S. patent application Ser. No. 13/024,642, filed Feb. 10, 2011, now granted as U.S. Pat. No. 8,282,621, which is a continuation of U.S. patent application Ser. No. 11/231,293, filed Sep. 21, 2005, now granted as U.S. Pat. No. 7,909,809, which claims the benefit of priority under 35 U.S.C. § 119 to U.S. Provisional Application Ser. No. 60/612,797, filed Sep. 27, 2004, the disclosures of which are herein incorporated herein by reference in their entirety.

FIELD OF THE INVENTION

This invention relates to medical devices and related methods thereof. In a particular embodiment, this invention relates to devices and related methods for performing agent-assisted endoscopic procedures in, for example, a gastrointestinal (GI) tract of a patient.

DESCRIPTION OF RELATED ART

An endoscope is a medical device that enables viewing of the interior of a body cavity or hollow organ without employing invasive surgical procedures. The endoscope includes an elongated flexible tube having a suitable imaging device at its distal end portion. This tube may be inserted through a naturally occurring opening, such as the esophagus or rectum, or through a small incision surgically made in the body. Suitable surgical instruments may be passed through the tube to perform various medical procedures, such as, for example, tissue sampling or removal of diseased tissue or polyps.

Endoscopic procedures are commonly used for diagnosis and/or treatment of the GI tract. For example, an endoscopic procedure may be performed to take tissue samples from the GI tract for pathological evaluation and/or therapeutic purposes. For example, with advances in the imaging technology, endoscopic procedures may be used to accurately detect and remove pre-cancerous mucosal tissue or tumors from various locations in the GI tract.

Currently, interventional endoscopists perform fluid-assisted polypectomy, endoscopic mucosal resection (EMR), and endoscopic submucosal dissection (ESD) procedures to remove pre-cancerous mucosal tissue from the GI tract. Such a fluid-assisted procedure may involve Injecting a saline fluid cushion between the mucosal and submucosal tissue layers so as to raise or separate the target mucosal tissue layer from the submucosal tissue layer in order to safely perform the procedure (e.g., by preventing or reducing risks of perforating the GI tract).

Currently available fluids for this purpose, however, dissipate quickly and therefore cannot provide a long lasting cushioning effect for the entire duration of the procedure. For example, sterile saline, which is the most commonly used fluid, typically provides a suitable cushion for only about 3 to 5 minutes. When the fluid is dissipated, the endoscopist must re-inject the fluid to assure the target tissue layer remains raised or bulked. The more times the tissue is pierced with an injection needle to inject the fluid, the more holes that are created for the fluid to leak out Although there are fluids that last longer than the sterile saline, such as hydroxypropyl methyl cellulose and hyaluronic acid, these fluids are merely more viscous so as not to flow as quickly as the less viscous fluids do. Nevertheless, these fluids usually provide a suitable cushion for only about 30 minutes, and are much more difficult to inject through the injection device because they require higher Injection pressure due to their higher viscosities.

SUMMARY OF THE INVENTION

Therefore, various embodiments of the invention relate to bulking or cushioning agents or other like materials for use in medical procedures, such as a fluid- or agent-assisted endoscopic procedure, and related methods of using those agents or materials in such a procedure. According to embodiments, the agents or material may be easy to inject, stable for the duration of the entire procedure (e.g., typically lasting from about 30 minutes to about 12 hours), and/or easy to remove when the agent or material is no longer needed. While an embodiment of the present invention will be described in connection with an endoscopic procedure (i.e., tissue resection) in the GI tract, embodiments of the invention may be used in other suitable'endoscopic procedures or applied to different parts of a body, other than the GI tract. Embodiments of the invention may also be applied to numerous procedures other than the endoscopic procedures, such as urologic procedures, plastic surgeries, or open invasive surgeries.

To attain the advantages and in accordance with the purpose of the invention, as embodied and broadly described herein, one aspect of the invention may provide a method of performing a medical procedure in a tract of a body. The method may include injecting a material in a liquid phase proximate a target site between a first tissue layer and a second tissue layer, where the material may have the liquid phase at temperatures below a predetermined temperature and a gel phase at temperatures approximately at or above the predetermined temperature. The method may further include allowing the material to transition from the liquid phase to the gel phase in response to a raise in temperature of the material to approximately at or above the predetermined temperature, and performing a surgical procedure on the target site.

According to another aspect of the invention, the method may include removing the material from the target site. Removing the material may include injecting a cold fluid into the target site In contact with the material, allowing the material to transition from the gel phase to the liquid phase. In still another aspect, performing a surgical procedure may include removing tissue from the target site. In still yet another aspect of the invention, the method may further may include positioning an endoscope In the vicinity of a target site.

In various aspects of the invention, the predetermined temperature may be a temperature of the body.

In another aspect, the material may include polyoxyethylene-polyoxyproplyene block copolymers. The molecular weights of the block copolymers may range from approximately 5,000 to approximately 25,000.

According to still another aspect of the invention, the material may remain in the gel phase for at least approximately 30 minutes.

In an aspect, the material may raise the first tissue layer. In another aspect of the invention, the first tissue layer may be a mucosal tissue layer, and the second tissue layer may be a submucosal tissue layer. In still another aspect, the tract may be a gastrointestinal tract.

In various aspects, the material may comprise poly(n-isopropyl acrylamide). Alternatively or additionally, the material may comprise thermally sensitive inorganic-organic hybrid gels or block copolymer. The thermally sensitive block copolymer may comprise poly(N-isopropyl acrylamide-b-dl-lactide). The material may comprise polyvinyl alcohol. The material may be configured to be responsive to a change in its pH level.

An aspect of the invention may provide a method of performing a medical procedure in a tract of a body. The method may Include injecting a material in a liquid phase proximate a target site between a first tissue layer and a second tissue layer, the material having the liquid phase at pH levels below a predetermined pH level and having a gel phase at pH levels approximately at or above the predetermined pH level. The method may further include allowing the material to transition from the liquid phase to the gel phase in response to a raise in pH of the material to approximately at or above the predetermined pH level, and performing a surgical procedure on the target site.

Another aspect of the invention may provide a system for performing a medical procedure. The system may Include an elongated member having a sharp distal end configured to pierce through tissue and a cushioning material contained in the elongated member and configured to flow out of the distal end of the elongated member. The material may have a liquid phase at temperatures below a predetermined temperature and have a gel phase at temperatures approximately at or above the predetermined temperature.

In still another aspect of the invention, the elongated member may comprise a syringe needle. Alternatively or additionally, the elongated member may comprise an elongated lumen connecting a proximal handle and the distal end. The cushioning material may be contained in the lumen. In yet still another aspect, the system may include an end effector for performing a surgical procedure. In an aspect, the system may also include a lumen extending from a fluid port In a proximal handle to the distal end.

Additional objects and advantages of the invention will be set forth in part in the description which follows, and in part will be obvious from the description, or may be learned by practice of the Invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various exemplary embodiments of the invention and together with the description, serve to explain the principles of the invention.

In the drawings.

DESCRIPTION OF THE EMBODIMENTS

Figure 3:
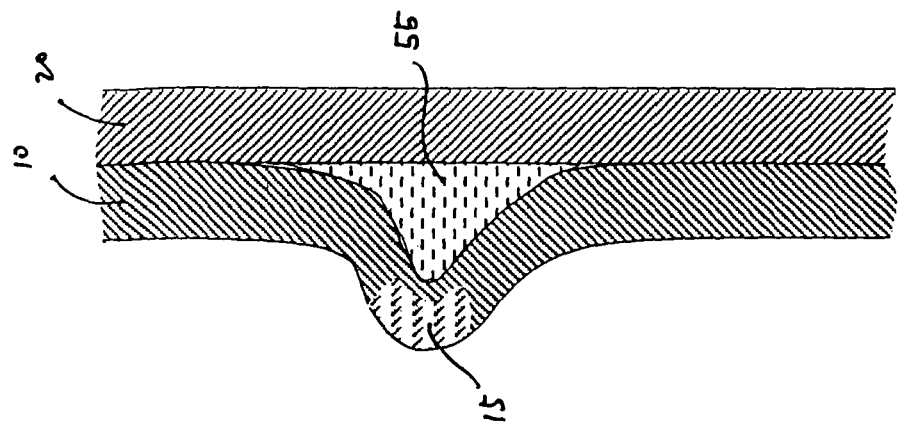
FIG. 3 is a schematic cross-sectional view of mucosal and submucosal tissue layers In the GI tract, showing the raised mucosal tissue layer resulting from the injection of the cushioning material.

Reference will now be made in detail to the exemplary embodiments of the invention, examples of which are illustrated in the accompanying drawings. Wherever possible, the same reference numbers will be used throughout the drawings to refer to the same or like parts.

In performing a fluid or other agent assisted, interventional endoscopic procedure in the GI tract, such as, for example, polypectomy, endoscopic mucosal resection (EMR), or endoscopic submucosal dissection (ESD), various exemplary embodiments of the invention may utilize a bulking or cushioning material that has characteristics of phase transformation or transition from a low viscosity state (e.g., liquid phase) into a high viscosity state (e.g., gel phase) in response to a predetermined temperature (e.g., body temperature).

Such a material may be referred to as a lower critical solution temperature (LCST) material, where the LCST refers to the temperature at which the transition from a liquid phase to a gel phase occurs. When the LCST material is injected into a body, the temperature of the LCST material may increase due to heat transfer from the body or other method of increasing the temperature of the surrounding environment. Once the temperature of the LCST material reaches the level of the LCST, the transition from the liquid phase to the gel phase may take place. The LCST may be a specific temperature or a range of temperatures. The LCST may be a material property and can be controlled by carefully selecting or preparing the LCST material to be used.

For example, the LCST material may be configured or prepared to remain in a liquid phase, with a low viscosity, at any temperature below the body temperature (i.e., ~37° C.), and to transform to a gel phase at or above the body temperature. Since the viscosity of the material in the liquid phase is low, the material can be injected into a body in a similar manner as is currently used for saline. Once the material is placed at a target site within a body, the material may become gelatinized or solidified due to the effect of the body temperature. In this phase, the material may remain in the injected location for the entire duration of the endoscopic procedure until it is removed from that location, thereby providing a more stable bulking or cushioning effect and eliminating the need for additional injection of material.

The LCST material may also be readily removed from the target site after an endoscopic procedure is completed. For example, due to the same characteristics of temperature-sensitive transition, cold water or saline may be injected into the target site so as to allow the temperature of the LCST material to decrease. The decrease in the temperature of the LCST material will change its phase from the gel phase back to the liquid phase, enabling it to be flushed away from the target site together with the injected cold water or saline.

Suitable LCST materials for use, according to various exemplary embodiments of the invention, may comprise polyoxyethylene-polyoxyproplyene (PEO-PPO) block copolymers. Two acceptable compounds may include Pluronic acid F127 and F108, which are PEO-PPO block copoloymers with molecular weights of 12,600 and 14,600, respectively. Each of these compounds may be available from BASF of Mount Olive, N.J. Other PEO-PPO block copolymers that have similar characteristics of LCST materials and are biocompatible and biodegradable, may also be used. In general, PEO-PPO block copolymers having molecular weights ranging, for example, between 5,000 and 25,000, and more particularly between 7,000 and 15,000, may be used.

In an exemplary embodiment, Pluronic acid F108 at 20-28% concentration in phosphate buffered saline (PBS) may be used as LCST material. Preferably, Pluronic acid F108 at 22.5% concentration In PBS may be used. A preparation of 22% Pluronic acid F108 in PBS has an LCST of approximately 37° C. In another exemplary embodiment, Pluronic acid F127 at 20-35% concentration in PBS may be used. By way of example, 20% Pluronic acid F127 in PBS has an LCST of approximately 37° C.

Other LCST materials appropriate for use, according to another exemplary embodiment of the invention, may include poly(N-isopropyl acrylamide) (PNIPAA). For example, temperature-responsive copolymer (or ternary copolymer) gels of N-Isopropyl acrylamide (IPAAm) may be synthesized with one or more comonomers (e.g., hydrophobic alkyl methacrylate (RMA), hydrophilic acrylamide (AAm), N,N'-dimethylacrylamide (DMAAm), and/or N-acryloylpyrrolidine (APy)) to control transition temperature and thermo-sensitivity of the gel.

For example, introduction of hydrophobic RMA may lower the LCST of poly (IPAAm) gel in PBS, and the change in material property (e.g., material rigidity, equilibrium swelling ratio, etc.) in response to temperature may become smaller with an increase of RMA content. In case the LCST material carries a therapeutic agent, RMA may be useful in regulating the release of the agent (e.g., due to RMA's hydrophobic interaction of alkyl chains) by controlling the temperature at which the agent may be released (e.g., on-off regulation) from the surface of the LCST material.

Introduction of AAm may increase the LCST of poly (IPAAm) gel, and the thermo-sensitivity of the gel may become smaller with an increase of AAm content. Hydrophilic AAm may prevent the formation of a dense skin layer (e.g., at the outer surface of the LCST material) at a higher temperature.

Introduction of DMAAm or APy may increase the LCST. DMAAm or APy may also increase the thermo-sensitivity of the LCST material, such that the material may effectively respond even in a small temperature change. This may be useful in enabling 'on-off' drug release responsive to smaller temperature changes in the body temperature range.

In still another exemplary embodiment, thermally sensitive inorganic-organic (hybrid) gels may be used. For example, the gels may be prepared by hybridizing porous silica and poly(N-isopropylacrylamide) gels (PNIPAAm gel). The internal pores of the silica may be filled with PNIPAAm gel to form a temperature-sensitive filler (e.g., drug reservoir). Alternatively or additionally, silica or other inorganic filler may be surface grafted with a temperature-sensitive polymer.

A thermally sensitive block copolymer, such as, for example, poly(N-isopropyl acrylamide-b-dl-lactide) (PIPAAm-PLA), may also be used. The polymer may be synthesized by ring-opening polymerization of dl-lactide, initiated from hydroxy-terminated poly (N-isopropylacrylamide) (PIPAAm). A PIPAAm, bearing a single terminal hydroxyl group, may be prepared by telomerization using 2-hydroxyethanethiol as a chain-transfer agent. Successful preparation of PIPAAm and the PIPAAm-PLA block copolymer may be verified by gel permeation chromatography (GPC) and $^1$H-NMR spectroscopy. Polymeric micelles may be prepared from block copolymers using a dialysis method. Their solutions may show reversible changes in optical properties, such as transparency below a LCST and opaque above the LCST. Dynamic light scattering measurements were used to observe the formation of micellar structures approximately 40 nm in diameter, which do not change between 20° C. and 30° C. Above the LCST, polymer micelles aggregated, a phenomenon found to be reversible since the aggregates dissociated again by cooling below the LCST.

Other LCST materials appropriate for use, according to various exemplary embodiments of the invention, may include, but are not limited to, degradable oligomers of Poloxamer 407 having either carbonate or urea linkages in the backbone structure, and Poloxamer 407.

Besides the LCST materials, according to various other exemplary embodiments of the invention, the cushioning or bulking materials may be configured to be responsive to other stimuli, such as pH or light. For example, the cushioning or bulking material may be injected in a flowable low-viscosity phase into a body where the material may be exposed to a predetermined pH level (e.g., 7.4 in the body). The low-viscosity material may then be mixed with a body fluid to change its pH level. The change in the pH level may change its phase from the flowable low-viscosity material to a more stable semi-rigid gel phase.

In various exemplary embodiments, the cushioning or bulking materials may be configured to be responsive to a combination of two or more stimuli. For example, the cushioning or bulking materials may be configured to be responsive to both temperature and pH level. Such a material may be useful for delivery of various forms of drugs because it may be desirable to be able to control delivery of various drugs (e.g., by increasing swelling of the material for diffusion-controlled release of a drug) without bringing the LCST above, for example, 37° C. Suitable materials may include, but are not limited to, N-isopropylacrylamide (NIP) polymerized with either Maleic Acid (MAc), which is a diprotic acid, or Acrylic Acid (AAc), which is a monoprotic acid.

In an exemplary sample tested, NIP polymerized with MAc (i.e., pNIP MAc) demonstrated greater swelling over NIP polymerized with AAc (i.e., pNIP AAc). The LCST increase for MAc was observed at a pH corresponding to deprotonation of almost all of the first acid groups. Further increases in pH led to deprotonation of the second —OH and only served to increase the charge concentration at a given location. These results may provide strong support for the theory that LCST results largely from uninterrupted chain lengths of NIP and that swelling results from actual charge density of acid groups along the chain.

In an alternative embodiment, a two-part mixed component that includes, for example, an expandable urethane foam may be used to lift or raise tissue during a medical procedure.

In still other exemplary embodiments, polyvinyl alcohol (PVA), gelatin particles, collagen, alginates, or any other embolic agents known in the art may be used as a bulking or cushioning material. For example, PVA-based or gelatin-based microspheres (500-900 µm) may be prehydrated in saline for injection into a target site.

Certain injection agents may be formulated as precursors to a cross-linked agent which may be formed in-situ. For example, calcium Ions may cross-link alginate, and dialdehyde (e.g., succindialdehyde, glutaraidehyde, carbodiimide, etc.) may cross-link collagen. If such precursors are injected together or mixed just prior to injection, the injection agent may set up in-situ. By cross-linking the precursors, the relative volumes or concentrations of the precursors may be altered to obtain the desired delivery and/or setup characteristics. In various alternative or additional embodiments, other suitable cross-linking agents known in the art may be used. For example, various energy sources (such as heat, radiation, ultrasound, light, etc.) may be used to cross-link the precursors.

In various exemplary embodiments, imaging agents, such as, for example, fluorescent dye, colorants, crystal violet, fillers, or any other agents known in the art, may be added to the bulking or cushioning material. In another exemplary embodiment, one or more therapeutic agents may be added so as to be delivered to the body with the material. For example, a cancer-treating agent, such as endostatin, may be added to the material. Other agents, such as, for example, hormones, anti-inflammatory agents, antibiotics, pain-relieving agents, antibacterial agents, and/or anti-fungal agents, may additionally or alternatively be added.

With reference to FIGS. 1-6, the methods and systems according to various exemplary embodiments of the invention will be described. As mentioned above, while an embodiment of the invention will be described in connection with a particular endoscopic procedure in the GI tract, embodiments of the invention may be used with other suitable endoscopic procedures, or for procedures other than the endoscopic procedures, such as urologic procedures, plastic surgeries, or open invasive surgeries. In addition, embodiments of the invention may be applied to numerous others parts of a body, different from the GI tract. In addition, while the embodiment of FIGS. 1-6 is described in connection with an LCST material, the method may be used with materials that transition from a fluid to a gel phase due to other stimuli such as a pH change.

FIGS. 1-6 are cross-sectional views of a portion in the GI tract showing the mucosal and submucosal tissue layers 10, 20, and illustrate a device and method for performing a fluid-assisted endoscopic resection of diseased tissue 15 in the mucosal tissue layer 10.

Figure 2:
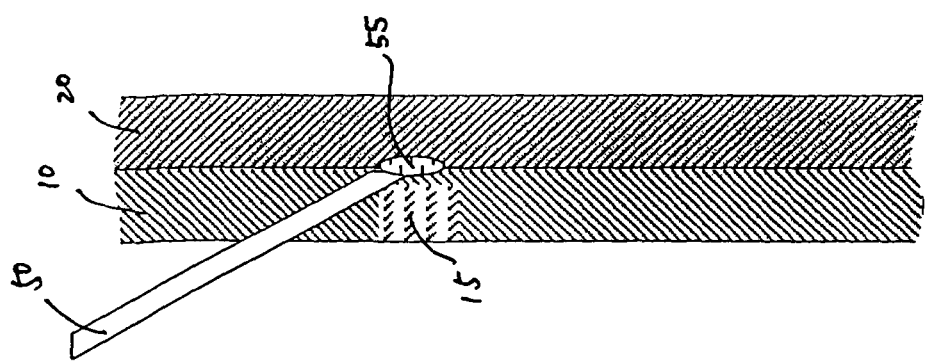
FIG. 2 is a schematic cross-sectional view of mucosal and submucosal tissue layers in the GI tract, illustrating an exemplary method step of injecting a bulking or cushioning material between the mucosal and submucosal tissue layers.
Figure 1:
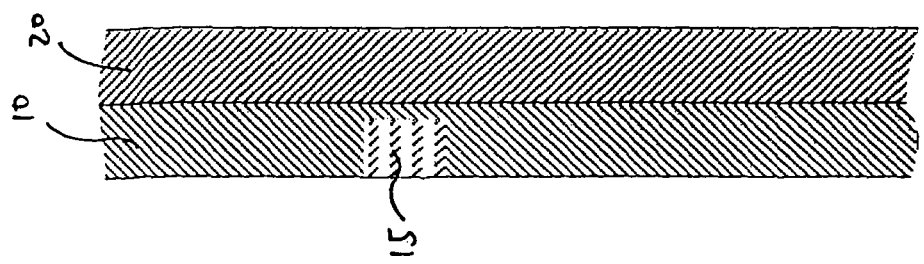
FIG. 1 is a schematic cross-sectional view of mucosal and submucosal tissue layers in a GI tract, showing diseased tissue in the mucosal tissue layer.

As shown in FIG. 2, the device may include an injection needle 50 that may be inserted into esophagus by any suitable means, such as through a lumen of an endoscope (not shown), so that its distal end portion may be positioned in the vicinity of a target site. The needle 50 may include a hollow lumen through which the LCST material 55 may flow. The distal end of the needle 50 may include a sharp edge configured to pierce through tissue layers 10, 20, so that the distal end of the needle 50 may be positioned between the mucosal tissue layer 10 and the submucosal tissue layer 20 to deliver the LCST material 55 therein. The amount of LCST material to be injected may depend on various factors, such as, for example, type of procedure performed, type of resection instrument used, size of the diseased tissue, or desired degree of bulking or cushioning.

Once the LCST material 55 is injected between the mucosal and submucosal tissue layers 10, 20, due to heat transfer from the body, the temperature of the LCST material 55 may rise to its LCST and transition to the gel phase. This may form a stable three-dimensional gel and provide a stable cushioning against a portion of the mucosal tissue layer 10 containing the diseased tissue 15, as shown in FIG. 3.

Figure 4:
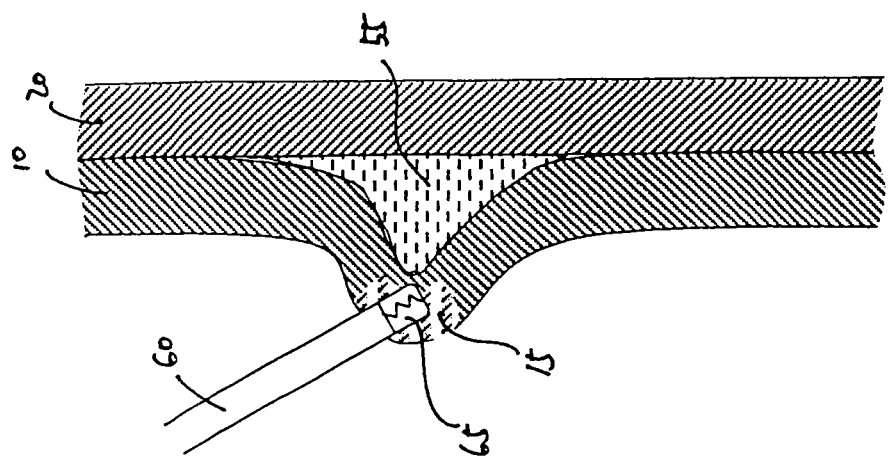
FIG. 4 is a schematic cross-sectional view of mucosal and submucosal tissue layers in the GI tract, illustrating an exemplary method step of removing diseased tissue from the mucosal tissue layer.

While the LCST material 55 remains in the gel state, a suitable endoscopic resection device 60 having a suitable cutting member 65 (e.g., biopsy forceps, snare, scissors, etc.) may be used to remove the diseased tissue 15 from the mucosal tissue layer 10, as shown in FIG. 4. The device 60 may be delivered to the tissue site by any suitable means known in the art, such as through a lumen of an endoscope. The LCST material 55 may maintain its stable three-dimensional shape throughout the procedure. The material 55 may stay in place even if the cushioned portion 19 is torn or ruptured due to the tissue-removing procedure, as shown in FIG. 5.

Figure 6:
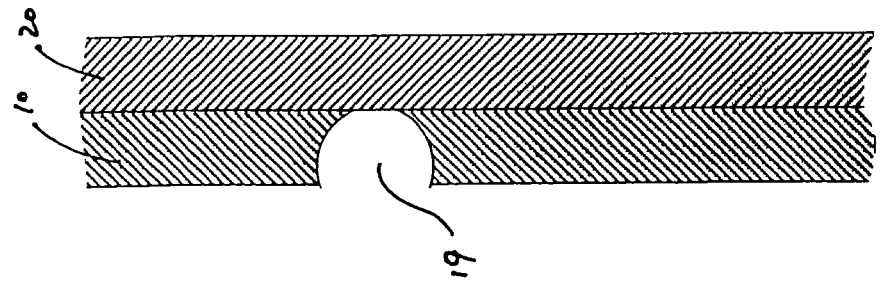
FIG. 6 is a schematic cross-sectional view of mucosal and submucosal tissue layers in the GI tract, showing the condition of the mucosal and submucosal tissue layers after the endoscopic procedures.
Figure 5:
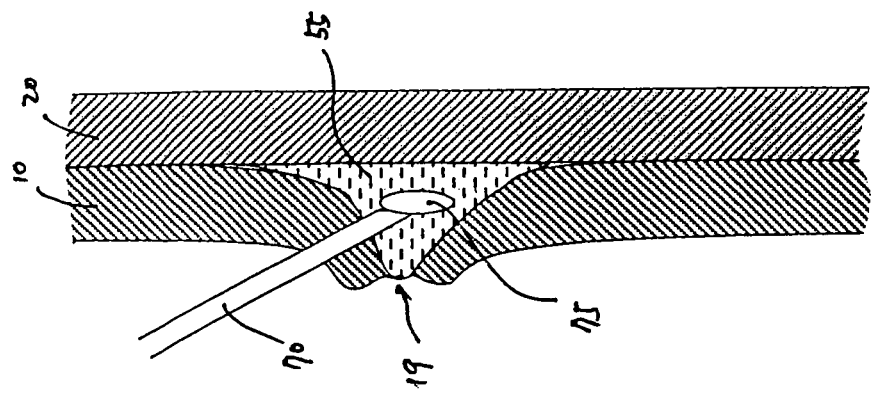
FIG. 5 is a schematic cross-sectional view of mucosal and submucosal tissue layers in the GI tract, illustrating an exemplary method step of removing the bulking or cushioning material from the mucosal and submucosal tissue layers.

To remove the LCST material 55 after the diseased tissue is fully removed or otherwise treated, cold water or saline 75 may be injected via a suitable injection needle 70 (which may be the same needle 50 used to inject the LCST material) into the cushioned portion so that the temperature of the LCST material 55 may fall below its LCST, as shown in FIG. 5, causing the phase change from the gel phase back to the liquid phase. The LCST material 55 may then be readily washed away from the site with the injected water or saline 75. Alternatively, if the LCST material 55 is made of a bioabsorbable material, the material 55 may be left in place until it naturally dissolves away by itself. FIG. 6 shows the portion of the mucosal and submucosal tissue layers after the above-described endoscopic procedure is completed.

While the figures show that the diseased tissue 15 Is located in the mucosal tissue layer 10, a similar device and method may be used for cases where the diseased tissue 15 is located in the submucosal tissue layer 20.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claims is:

1. A method of performing a medical procedure at a target site comprising a first tissue and a second tissue, comprising:
   injecting a material at the target site between the first tissue and the second tissue, thereby separating the first tissue from the second tissue, the material transitioning from a first viscosity to a second viscosity upon injection, the second viscosity being greater than the first viscosity; and
   performing the medical procedure at the target site.

2. The method of claim 1, wherein the medical procedure is performed on diseased tissue at the target site.

3. The method of claim 1, wherein the medical procedure is a tissue resection or a tissue dissection.

4. The method of claim 1, wherein the medical procedure is an endoscopic procedure.

5. The method of claim 1, wherein the medical procedure is performed in the gastrointestinal tract.

6. The method of claim 1, wherein the medical procedure includes endoscopic mucosal resection or endoscopic submucosal dissection.

7. The method of claim 1, wherein the medical procedure is a urological procedure and the material is a bulking or cushioning agent.

8. The method of claim 1, wherein the material includes a therapeutic agent and/or an imaging agent.

9. A method of performing a medical procedure at a target site comprising a first tissue and a second tissue, comprising:
   injecting a material at the target site between the first tissue and the second tissue, the material transitioning from a first viscosity to a second viscosity upon injection, the second viscosity being greater than the first viscosity; and
   performing the medical procedure at the target site;
   wherein the material creates spacing between the first tissue and the second tissue prior to performing the medical procedure at the target site.

10. The method of claim 9, wherein the medical procedure is performed on diseased tissue at the target site.

11. The method of claim 9, wherein the medical procedure includes removing tissue from the target site.

12. The method of claim 9, wherein the medical procedure is a tissue resection or a tissue dissection.

13. The method of claim 9, wherein the medical procedure includes endoscopic mucosal resection or endoscopic submucosal dissection.

14. The method of claim 9, wherein the medical procedure is a urological procedure.

15. The method of claim 9, wherein the material includes a therapeutic agent and/or an imaging agent.

16. A method of performing a medical procedure at a target site comprising a first tissue and a second tissue, comprising:
   injecting a material at the target site, thereby creating spacing between the first tissue and the second tissue, the material transitioning from a first viscosity to a second viscosity upon injection, the second viscosity being greater than the first viscosity; and
   performing the medical procedure at the target site.

17. The method of claim 16, wherein the medical procedure is performed on diseased tissue at the target site.

18. The method of claim 16, wherein the medical procedure is a tissue resection.

19. The method of claim 16, wherein the medical procedure is a tissue dissection.

20. The method of claim 16, wherein the material includes a therapeutic agent and/or an imaging agent.

* * * * *